United States Patent
Nebel et al.

(10) Patent No.: US 11,123,275 B2
(45) Date of Patent: Sep. 21, 2021

(54) HIGH-PERFORMANCE HAIR TREATMENT AGENTS WITH INCREASED CARE EFFECT

(71) Applicant: Henkel AG & Co. KGaA, Duesseldorf (DE)

(72) Inventors: Monika Nebel, Henstedt Ulzburg (DE); Erik Schulze zur Wiesche, Hamburg (DE)

(73) Assignee: HENKEL IP & HOLDING GMBH, Duesseldorf (DE)

( * ) Notice: Subject to any disclaimer, the term of this patent is extended or adjusted under 35 U.S.C. 154(b) by 0 days.

(21) Appl. No.: 16/115,130

(22) Filed: Aug. 28, 2018

(65) Prior Publication Data

US 2019/0060198 A1 Feb. 28, 2019

(30) Foreign Application Priority Data

Aug. 29, 2017 (DE) .................... 10 2017 215 071.8

(51) Int. Cl.
| | | |
|---|---|---|
| *A61K 8/42* | (2006.01) | |
| *A61Q 5/12* | (2006.01) | |
| *A61Q 5/02* | (2006.01) | |
| *A61K 8/34* | (2006.01) | |
| *A61K 8/44* | (2006.01) | |
| *A61K 8/65* | (2006.01) | |
| *A61Q 5/00* | (2006.01) | |
| *A61K 8/41* | (2006.01) | |

(52) U.S. Cl.
CPC ............... *A61K 8/42* (2013.01); *A61K 8/347* (2013.01); *A61K 8/442* (2013.01); *A61K 8/65* (2013.01); *A61Q 5/002* (2013.01); *A61Q 5/02* (2013.01); *A61Q 5/12* (2013.01); *A61K 2800/48* (2013.01); *A61K 2800/5426* (2013.01); *A61K 2800/594* (2013.01); *A61K 2800/5922* (2013.01)

(58) Field of Classification Search
CPC ................. A61K 8/65; A61K 2800/48; A61K 2800/5426; A61K 2800/5922; A61K 2800/594; A61K 8/347; A61K 8/42; A61K 8/442; A61K 8/416; A61Q 5/12; A61Q 5/002; A61Q 5/02
See application file for complete search history.

(56) References Cited

U.S. PATENT DOCUMENTS

| | | | |
|---|---|---|---|
| 7,842,100 B2 * | 11/2010 | Matsunaga | A61K 8/361 8/405 |
| 2001/0036448 A1 * | 11/2001 | Pereira | A61Q 5/12 424/70.28 |
| 2010/0028271 A1 * | 2/2010 | Knappe | A61K 8/8158 424/47 |
| 2010/0278769 A1 | 11/2010 | Anderson et al. | |
| 2011/0253161 A1 | 10/2011 | Obukowho et al. | |

FOREIGN PATENT DOCUMENTS

| | | | |
|---|---|---|---|
| EP | 1181003 B1 | 2/2002 | |
| EP | 1927344 A1 | 6/2008 | |
| EP | 2151233 A1 | 2/2010 | |
| JP | H1 1292739 A | 10/1999 | |
| WO | WO 2013/091994 A1 * | 6/2013 | ............. A61K 31/20 |

OTHER PUBLICATIONS

Machine Translation for WO 2013/091994 A1; Rolf et al.; published Jun. 2013.*
Crawford, Holly; Good Housekeeping; "Your 9 Biggest Questions—Answered!"; published Jul. 2, 2014.*
Intellectual Property Office, Search Report under Section 17(5) for United Kingdom Patent Application No. GB1813764.6 dated Feb. 28, 2019.

* cited by examiner

*Primary Examiner* — Jeffrey T. Palenik
(74) *Attorney, Agent, or Firm* — Lorenz & Kopf, LLP

(57) ABSTRACT

The split end-reducing effect of anteiso fatty acid quats can be further enhanced by alkyldimethylammonium hydroxypropyl hydrolyzed keratin so that hair treatment agents containing at least one anteiso fatty acid quat and alkyldimethylammonium hydroxypropyl hydrolyzed keratin are particularly effective in reducing split ends.

1 Claim, No Drawings

HIGH-PERFORMANCE HAIR TREATMENT AGENTS WITH INCREASED CARE EFFECT

CROSS-REFERENCE TO RELATED APPLICATION

This application claims priority to German Patent Application No. 10 2017 215 071.8, filed Aug. 29, 2017, which is incorporated herein by reference in its entirety.

The present disclosure relates to hair treatment agents, in particular shampoos and so-called conditioners, having a combination of active ingredients for gentle and effective care of the hair.

Last but not least, the importance of care products with the longest possible effect increases through heavy stress of the hair, for example, by dyeing or perming and by cleaning the hair with shampoos and by environmental pollution. Such care products affect the natural structure and properties of the hair. Thus, for example, the wet and dry combability of the hair, the hold and the fullness of the hair can be optimized or the hair can be protected from increased split ends following such care treatments.

It has therefore long been customary to subject hair to a special after-treatment. In this case, the hair is treated with special active ingredients, for example quaternary ammonium salts or special polymers, sometimes in the form of a rinse. Depending on the formulation, this treatment improves the combability, the hold and the fullness of the hair and reduces the rate of split ends.

Nourishing ingredients in shampoos and conditioners are sometimes cationic in nature. The use of so-called quaternary anteiso fatty acid ammonium compounds ("anteiso fatty acid quats") is disclosed, for example, in EP 1 181 003 B1, in which the quaternized derivatives of 18-methyl-eicosanoic acid (18-MEA) are found to be particularly suitable.

Such quaternized derivatives of 18-methyl-eicosanoic acid (18-MEA) are marketed, for example, as Incroquat® 18-MEA-40 from Croda and designated as C10-40 isoalkylamidopropylethyldimonium ethosulfate in the INCI nomenclature. Products that contain corresponding ingredients are well established in the marketplace. The combination of this ingredient with hydrolyzed keratin is available on the market as a shampoo and conditioner.

BRIEF SUMMARY

It has now been found that the split end-reducing effect of anteiso fatty acid quats can be further increased by alkyldimethylammonium hydroxypropyl hydrolyzed keratin.

A first subject matter of the present disclosure are hair treatment agents containing
a) at least one anteiso fatty acid quat,
b) alkyldimethylammonium hydroxypropyl hydrolyzed keratin.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description Hair treatment agents for the purposes of the present disclosure are, for example, hair shampoos, hair conditioners, conditioning shampoos, hair sprays, hair rinses, hair treatments, hair wraps, hair tonics, perming-fixing solutions, hair dye shampoos, hair dyes, hair fixatives, hair dressings, hairstyling preparations, hair lotions, mousses, hair gels, hair waxes or combinations thereof. In view of the fact that, in particular, men sometimes shy away from the use of several different products and/or several application steps, consideration is given to such products which the man applies anyway. Exemplary products are therefore shampoos, conditioners or hair tonics.

The hair treatment agents contain at least one anteiso fatty acid quat. Anteiso refers to the third from last position in the hydrocarbon chain of branched fatty acids. Branched fatty acids occur in two forms in the vast majority: Iso fatty acids have a branched methyl group on the penultimate (=penultima), anteiso fatty acids have a methyl group on the ante-penultimate (=antepenultima) carbon atom of the main chain. Such corresponding fatty acids or their derivatives (anteiso fatty acid esters or anteiso fatty acid amides) are quaternized, for example by quaternization of a nitrogen atom.

In exemplary embodiments of the present disclosure, the anteiso fatty acid quat(s) is/are used within certain ranges of amounts. Here, exemplary hair treatment agents are exemplified by containing, based on their weight, a total amount from about 0.0001 to about 20% by weight, for example from about 0.0005 to about 15% by weight, such as from about 0.0075 to about 10% by weight, and in one embodiment from about 0.01 to about 2% by weight, of anteiso fatty acid quat(s).

Some consideration is given to the performance properties of anteiso fatty acid quats which are derived from substituted acid amides of anteiso fatty acids. These have a high effectiveness in hair conditioning and are also excellent in compatibility with other ingredients of hair treatment agents, so that the resulting agents have very good storage stability.

Exemplary hair treatment agents as contemplated herein contain, based on their weight, from about 0.0001 to about 20% by weight, for example from about 0.005 to about 15% by weight, such as from about 0.005 to about 10% by weight and in one embodiment from about 0.01 to about 2% by weight, of anteiso-fatty acid quat(s) of the formula (I)

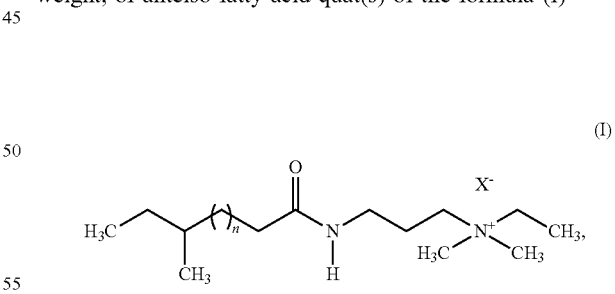

in which n stands for an integer from about 1 to about 34, for example from about 5 to about 19, in an example from about 7 to about 17 and in one embodiment from about 9 to about 15.

Exemplary hair treatment agents as contemplated herein contain, based on their weight, from about 0.0001 to about 20% by weight, for example from about 0.005 to about 15% by weight, such as from about 0.005 to about 10% by weight and in one embodiment from about 0.01 to about 2% by weight, of anteiso-fatty acid quat(s) of the formula (Ia)

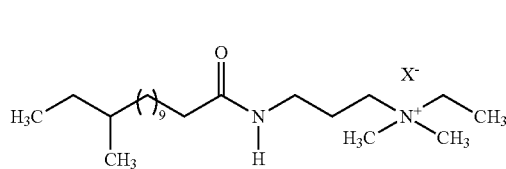

(Ia)

Exemplary hair treatment agents as contemplated herein contain, based on their weight, from about 0.0001 to about 20% by weight, for example from about 0.005 to about 15% by weight, such as from about 0.005 to about 10% by weight and in one embodiment from about 0.01 to about 2% by weight, of anteiso-fatty acid quat(s) of the formula (Ib)

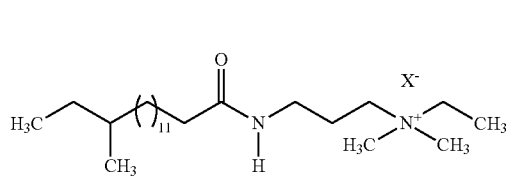

(Ib)

Exemplary hair treatment agents as contemplated herein contain, based on their weight, from about 0.0001 to about 20% by weight, for example from about 0.005 to about 15% by weight, such as from about 0.005 to about 10% by weight and in one embodiment from about 0.01 to about 2% by weight, of anteiso-fatty acid quat(s) of the formula (Ib)

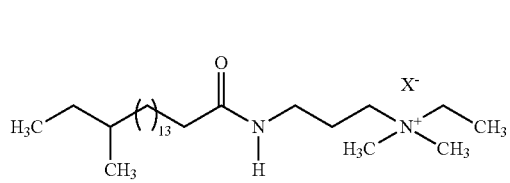

(Ic)

Exemplary hair treatment agents as contemplated herein contain, based on their weight, from about 0.0001 to about 20% by weight, for example from about 0.005 to about 15% by weight, such as from about 0.005 to about 10% by weight and in one embodiment from about 0.01 to about 2% by weight, of anteiso-fatty acid quat(s) of the formula (Ib)

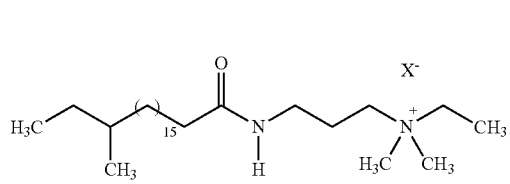

(Id)

Some exemplary hair treatment agents as contemplated herein contain, based on their weight, from about 0.0001 to about 20% by weight, for example from about 0.01 to about 15% by weight, such as from about 0.05 to about 10% by weight and in one embodiment from about 0.01 to about 2% by weight, of a mixture of anteiso fatty acid quats which bear the INCI name C10-40 isoalkylamidopropylethyldimonium ethosulfate and quaternized 18-methyl-eicosanoic acid (18-MEA) of the formula (II).

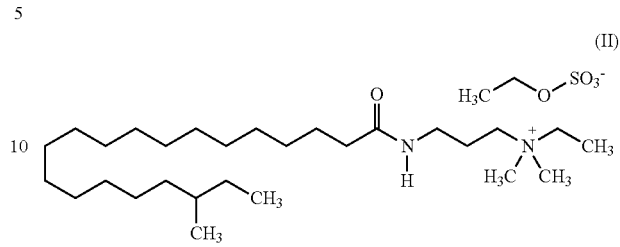

(II)

A corresponding product has been marketed by Croda under the name Incroquat® 18-MEA 40; recently, the corresponding mixture is marketed under the name Cutissential® 18-MEA 40.

As a second ingredient, the hair treatment agents as contemplated herein contain alkyldimethylammonium hydroxypropyl hydrolyzed keratin. These are cationic derivatives of keratin hydrolysates Exemplary hair treatment agents as contemplated herein contain, based on their weight, from about 0.0001 to about 20% by weight, for example from about 0.005 to about 15% by weight, such as from about 0.0075 to about 10% by weight and in one embodiment from about 0.01 to about 2% by weight, of alkyldimethylammonium hydroxypropyl hydrolyzed keratin.

The alkyl radicals in the alkyldimethylammonium hydroxypropyl hydrolyzed keratin used as contemplated herein contain from about 10 to about 24, such as from about 10 to about 22, even such as from about 12 to about 20 and in one embodiment from about 12 to about 18 carbon atoms.

Sometimes, corresponding products are synthesized from native fats and oils, so that exemplary hair treatment agents as contemplated herein are exemplified by containing, based on their weight, from about 0.0001 to about 20% by weight, for example from about 0.0005 to about 15% by weight, such as from about 0.0075 to about 10% by weight and in one embodiment from about 0.01 to about 2% by weight, of cocodimonium hydroxypropyl hydrolyzed keratin.

Further exemplary hair treatment agents as contemplated herein are exemplified by containing, based on their weight, from about 0.0001 to about 20% by weight, for example from about 0.0005 to about 15% by weight, such as from about 0.0075 to about 10% by weight and in one embodiment from about 0.01 to about 2% by weight, of steardimonium hydroxypropyl hydrolyzed keratin.

It is exemplary as contemplated herein, in view of a particularly pronounced split reduction, to use the ingredients a) and b) of the agents as contemplated herein in certain amount proportions relative to one another. Here, hair treatment agents as contemplated herein are exemplary in which the weight ratio of anteiso fatty acid quat(s) to alkyldimethylammonium hydroxypropyl hydrolyzed keratin(s) is from about 5:1 to about 1:5, for example from about 3:1 to about 1:3, such as from about 2:1 to about 1:2, even such as from about 1.5:1 to about 1:1.1 and in one embodiment from about 1.2:1 to about 1:1.

The hair treatment agents as contemplated herein may contain further ingredients.

Exemplary hair treatment agents contain at least one fatty alcohol.

Fatty alcohols are aliphatic, long-chain, monohydric primary alcohols having hydrocarbon radicals which have from about 6 to about 30, for example from about 6 to about 22, carbon atoms. The hydrocarbon radicals may be saturated or mono- or polyunsaturated. Exemplary fatty alcohols used in the context of the present disclosure are selected from 1-hexanol, 1-heptanol, 1-octanol, 1-decanol, 1-dodecanol (lauryl alcohol), 1-tetradecanol (myristyl alcohol) 1, 1-hexadecanol (cetyl alcohol), 1-heptadecanol (margaryl alcohol), 1-octadecanol (stearyl alcohol), 1-icosanol (arachidyl alcohol), 1-docosanol (behenyl alcohol), 1-tetracosanol (lignoceryl alcohol), 1-hexacosanol (ceryl alcohol), 1-octacosanol (montanyl alcohol), 1-triacontanol (melissyl alcohol), cis-9-hexadecen-1-ol (palmitoleyl alcohol), cis-9-octadecen-1-ol (oleyl alcohol), trans-9-octadecene-1-ol (elaidyl alcohol), cis-11-octadecene 1-ol, 6,9,12-octadecatrien-1-ol (γ-linolenyl alcohol) and mixtures thereof.

Particularly exemplary hair treatment agents are exemplified in that they contain, based on their weight, from about 0.1 to about 20% by weight, for example from about 0.5 to about 15% by weight, such as from about 1 to about 10% by weight and in one embodiment from about 2 to about 8% by weight, of fatty alcohol(s) of the formula (III)

$$H_3C-(CH_2)_k-CH_2-OH \quad (III)$$

in which k stands for integers from about 4 to about 28, for example from about 6 to about 24, such as from about 8 to about 22 and in one embodiment about 10, about 12, about 14, about 16, about 18 or about 20.

Particularly exemplary hair treatment agents as contemplated herein contain, based on their weight, from about 0.1 to about 20% by weight, for example from about 0.5 to about 15% by weight, such as from about 1 to about 10% by weight and in one embodiment from about 2 to about 8% by weight, of alcohol(s) from the group of 1-dodecanol (lauryl alcohol), 1-hexadecanol (cetyl alcohol), 1-octadecanol (stearyl alcohol), 1-docosanol (behenyl alcohol), wherein the amounts are based on the total amount of said fatty alcohols in the composition.

Some exemplary hair treatment agents as contemplated herein contain, based on their weight, from about 0.1 to about 20% by weight, for example from about 0.5 to about 15% by weight, such as from about 1 to about 10% by weight and in one embodiment from about 2 to about 8% by weight, of alcohol(s) from the group 1-hexadecanol (cetyl alcohol), 1-octadecanol (stearyl alcohol), wherein the amounts are based on the total amount of said fatty alcohols in the composition.

Hair treatment agents as contemplated herein, which are formulated as conditioners or as care shampoos, for example contain at least one cationic surfactant.

The cationic surfactant(s) is selected from the group of quaternary ammonium compounds and/or amidoamines wherein exemplary cationic surfactant(s) is/are selected from
alkyltrimethylammonium chlorides having from about 10 to about 18 carbon atoms in the alkyl radical and/or
dialkyltrimethylammonium chlorides having from about 10 to about 18 carbon atoms in the alkyl radical and/or
tridialkyltrimethylammonium chlorides having from about 10 to about 18 carbon atoms in the alkyl radical and/or
cetyltrimethylammonium chloride and/or
stearyltrimethylammonium chloride and/or
behenyltrimethylammonium chloride and/or
distearyldimethylammonium chloride and/or
lauryldimethylammonium chloride and/or
lauryldimethylbenzylammoniumchlorid and/or
tricetylmethylammonium chloride
quaternium-27 and/or
quaternium-83.

As contemplated herein exemplary hair treatment agents contain, based on their weight, from about 0.05 to about 20% by weight, for example from about 0.1 to about 10% by weight, such as from about 0.25 to about 8% by weight and in one embodiment from about 0.5 to about 7% by weight, of cationic surfactant(s).

Particularly exemplary cationic surfactants are selected from compounds of the following formula (IV)

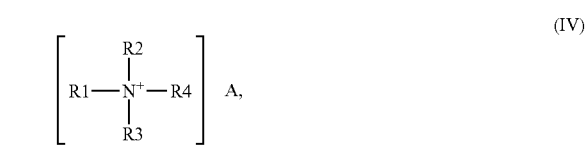

in which at most three radicals R1 to R4 independently of one another stand for a saturated or unsaturated, branched or unbranched alkyl group having from about 1 to about 4 C atoms, at least one radical R1 to R4 for a saturated or unsaturated, branched or unbranched alkyl chain having from about 8 to about 30 C atoms, and A means a physiologically compatible organic or inorganic anion, In exemplary compounds according to formula (IV), two or three radicals R1 to R4 stand for a methyl or an ethyl group, one or two radical(s) R1 to R4 stand for a saturated or unsaturated, branched or unbranched alkyl chain having from about 14 to about 26 carbon atoms, and A stands for a halide ion, a sulfate of the general formula $RSO_3^-$, in which R has the meaning of saturated or unsaturated alkyl radicals having from about 1 to about 4 carbon atoms, or for an anionic radical of an organic acid such as maleic acid, fumaric acid, oxalic acid, tartaric acid, citric acid, lactic acid or acetic acid.

More exemplary are compounds according to formula (IV) in which three radicals R1 to R4 stand for a methyl group, a radical R1 to R4 stands for a cetyl, palmityl, stearyl, arachidyl or a behenyl group, and A stands for a chloride or a methosulfate ion.

With particular consideration, the at least one compound of the formula (IV) is selected from cetyltrimethylammonium chloride, cetyltrimethylammonium methosulfate, behentrimethylammonium chloride and/or behentrimethylammonium methosulfate. These compounds can be used in the agent as contemplated herein individually or in their combination, wherein the total amount of compounds of formula (I) in the agent is at most about 10% by weight, and wherein the amount specification refers to the total weight of the agent as contemplated herein.

With particular consideration, an agent as contemplated herein contains behenium trimethyl ammonium chloride as cationic surfactant. Here, hair treatment agents as contemplated herein which are exemplary contain, based on their weight, from about 0.05 to about 20% by weight, for example from about 0.1 to about 10% by weight, such as from about 0.25 to about 8% by weight and in one embodiment from about 0.5 to about 7% by weight, of behenyl trimethyl ammonium chloride.

The hair treatment agents can also contain at least one esterquat as a cationic surfactant.

For the purposes of the present disclosure, "esterquats" are understood as meaning compounds according to the following formula (V)

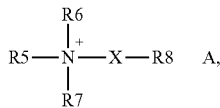
(V)

in which
each of R5, R6 and R7 may independently be the same or different from one another and have the following meaning:
  a saturated or unsaturated, branched or unbranched alkyl radical having from about 1 to about 4 carbon atoms, which may contain at least one hydroxyl group, or
  a saturated or unsaturated, branched or unbranched or a cyclic saturated or unsaturated alkyl radical having from about 6 to about 30 carbon atoms, which may contain at least one hydroxyl group, or
  an aryl or alkylaryl radical, for example, phenyl or benzyl, or
  (—X—R8), with the stipulation that at most about 2 of the radicals R5, R6 or R7 can stand for (—X—R8), wherein
X has the following meaning:
  —(CH2)n- with n=from about 1 to about 20, for example n=from about 1 to about 10 and in an example n=from about 1-about 5, or
  —(CH$_2$—CHR9 O)$_n$— with n=from about 1 to about 200, for example from about 1 to about 100, such as from about 1 to about 50, and in an example from about 1 to about 20, and with R9 in the meaning of hydrogen, methyl or ethyl, or
  a hydroxyalkylene group having one to four carbon atoms, which may be branched or unbranched, and which contains at least one and at most about 3 hydroxyl groups, and wherein
R8 has the following meaning:
  R10-O—CO—, wherein R10 is a saturated or unsaturated, branched or unbranched or a cyclic, saturated or unsaturated alkyl radical having from about 6 to about 30 carbon atoms, which may contain at least one hydroxyl group, and which may furthermore be ethoxylated with from about 1 to about 100 ethylene oxide units and/or or from about 1 to about 100 propylene oxide units, or
  R11-CO—, wherein R11 is a saturated or unsaturated, branched or unbranched or a cyclic, saturated or unsaturated alkyl radical having from about 6 to about 30 carbon atoms, which may contain at least one hydroxyl group, and which may furthermore be ethoxylated with from about 1 to about 100 ethylene oxide units and/or or from about 1 to about 100 propylene oxide units, or
in which A stands for a physiologically compatible organic or inorganic anion, one of the radicals R5, R6 or R7 stands for the group (—X—R8), R8 stands for a nonethoxylated fatty acid radical, such as a palmitin, stearin, arachin or a behenic acid radical, in particular a stearic acid radical, and A stands for a halide ion, a sulfate ion of the general formula RSO$_3^-$, wherein R has the meaning of saturated or unsaturated alkyl radicals having from about 1 to about 4 carbon atoms, or for an anionic radical of an organic acid such as maleic acid, fumaric acid, oxalic acid, tartaric acid, citric acid, lactic acid or acetic acid, in particular for a chloride ion or for a methosulfate ion.

Esterquats suitable for agents of the present disclosure are selected from at least one of the products marketed under the trade names Rewoquat®, Stepantex®, Dehyquart®, Armocare® and Akypoquat®. Specific examples of particularly suitable esterquats as contemplated herein are the products Armocare® VGH-70, Dehyquart® F-75, Dehyquart® C-4046, Dehyquart® L80, Dehyquart® F-30, Dehyquart® AU-35, Rewoquat® WE18, Rewoquat®WE38 DPG, Stepantex® VS 90 and Akypoquat® 131.

Particular consideration is given to agents as contemplated herein which contain, as esterquat, at least one of the compounds known by the INCI names distearoylethyl hydroxyethylmonium methosulfate and distearoylethyl hydroxyethylmonium chloride.

Particular consideration is given to distearoylethyl hydroxyethylmonium methosulfate, which may be contained in the agents as contemplated herein in a exemplary amount from about 0.1 to about 10% by weight, such as from about 0.5 to about 8% by weight, in an example from about 0.75 to about 6% by weight and in one embodiment from about 1 to about 5% by weight, wherein the amount specifications are based on the total weight of the agent as contemplated herein.

The esterquat(s) can be added to the agents as contemplated herein either individually or as a mixture with other care ingredients.

On account of the better handleability and processability, it may be advantageous when the esterquat(s), in particular distearoylethyl hydroxyethylmonium methosulfate, is added to the agents as contemplated herein as an active ingredient mixture. A particularly suitable example of such an active ingredient mixture is available, for example, under the trade name Dehyquart® F 75 from BASF (distearoylethyl hydroxyethylmonium methosulfate and cetearyl alcohol).

The hair treatment agents contain at least one silicone, which ensures a pleasant feel of the hair and further enhances the split end-reducing effect of the combination as contemplated herein.

Exemplary agents as contemplated herein are exemplified in that they contain at least one silicone selected from:
  (i) polyalkyl siloxanes, polyaryl siloxanes, polyalkylaryl siloxanes which are volatile or nonvolatile, straight chain, branched or cyclic, crosslinked or uncrosslinked;
  (ii) polysiloxanes which contain in their general structure one or more organofunctional groups selected from:
    a) substituted or unsubstituted aminated groups;
    b) (per)fluorinated groups;
    c) thiol groups;
    d) carboxylate groups;
    e) hydroxylated groups;
    f) alkoxylated groups;
    g) acyloxyalkyl groups;
    h) amphoteric groups;
    i) bisulfite groups;
    j) hydroxyacylamino groups;
    k) carboxy groups;
    l) sulfonic acid groups; and
    m) sulfate or thiosulfate groups;
  (iii) linear polysiloxane (A)—polyoxyalkylene (B)—block copolymers of the type (A-B)$_n$ with n>about 3;
  (iv) grafted silicone polymers having a non-silicone organic backbone of an organic main chain formed from organic monomers which contain no silicone to which at least one polysiloxane macromer has been grafted in the chain and optionally at least one chain end;

(v) grafted polysiloxane backbone silicone polymers having grafted thereto non-silicone organic monomers having a polysiloxane backbone to which at least one organic macromer not containing silicone has been grafted in the chain and optionally at least at one of its ends;

or their mixtures.

Hair treatment agents which are exemplary as contemplated herein are exemplified in that they contain, based on their weight, from about 0.01 to about 20% by weight, for example from about 0.1 to about 10% by weight, such as from about 0.5 to about 7.5% by weight and in one embodiment from about 1 to about 5% by weight, of silicone(s).

Exemplary silicones are described below.

Particularly exemplary agents as contemplated herein are exemplified in that they contain at least one silicone of the formula Si-I

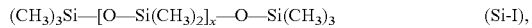

$(CH_3)_3Si—[O—Si(CH_3)_2]_x—O—Si(CH_3)_3$ (Si-I), in which x stands for a number from about 0 to about 100, for example from about 0 to about 50, such as from about 0 to about 20 and in one embodiment from about 0 to about 10.

These silicones are called DIMETHICONE according to the INCI nomenclature. In the context of the present disclosure, the compounds used are silicones of the formula Si—I:

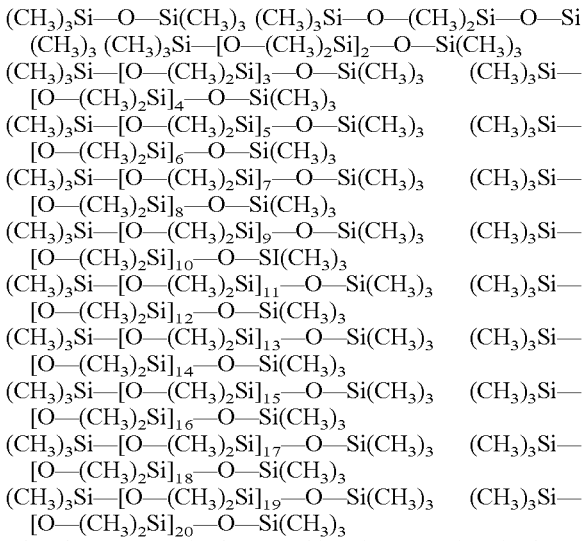

$(CH_3)_3Si—O—Si(CH_3)_3$ $(CH_3)_3Si—O—(CH_3)_2Si—O—Si(CH_3)_3$ $(CH_3)_3Si—[O—(CH_3)_2Si]_2—O—Si(CH_3)_3$
$(CH_3)_3Si—[O—(CH_3)_2Si]_3—O—Si(CH_3)_3$ $(CH_3)_3Si—[O—(CH_3)_2Si]_4—O—Si(CH_3)_3$
$(CH_3)_3Si—[O—(CH_3)_2Si]_5—O—Si(CH_3)_3$ $(CH_3)_3Si—[O—(CH_3)_2Si]_6—O—Si(CH_3)_3$
$(CH_3)_3Si—[O—(CH_3)_2Si]_7—O—Si(CH_3)_3$ $(CH_3)_3Si—[O—(CH_3)_2Si]_8—O—Si(CH_3)_3$
$(CH_3)_3Si—[O—(CH_3)_2Si]_9—O—Si(CH_3)_3$ $(CH_3)_3Si—[O—(CH_3)_2Si]_{10}—O—Si(CH_3)_3$
$(CH_3)_3Si—[O—(CH_3)_2Si]_{11}—O—Si(CH_3)_3$ $(CH_3)_3Si—[O—(CH_3)_2Si]_{12}—O—Si(CH_3)_3$
$(CH_3)_3Si—[O—(CH_3)_2Si]_{13}—O—Si(CH_3)_3$ $(CH_3)_3Si—[O—(CH_3)_2Si]_{14}—O—Si(CH_3)_3$
$(CH_3)_3Si—[O—(CH_3)_2Si]_{15}—O—Si(CH_3)_3$ $(CH_3)_3Si—[O—(CH_3)_2Si]_{16}—O—Si(CH_3)_3$
$(CH_3)_3Si—[O—(CH_3)_2Si]_{17}—O—Si(CH_3)_3$ $(CH_3)_3Si—[O—(CH_3)_2Si]_{18}—O—Si(CH_3)_3$
$(CH_3)_3Si—[O—(CH_3)_2Si]_{19}—O—Si(CH_3)_3$ $(CH_3)_3Si—[O—(CH_3)_2Si]_{20}—O—Si(CH_3)_3$ wherein $(CH_3)_3Si—O—Si(CH_3)_3$, $(CH_3)_3Si—O—(CH_3)_2Si—O—Si(CH_3)_3$ and/or $(CH_3)_3Si—[O—(CH_3)_2Si]_2—O—Si(CH_3)_3$ are particularly exemplary.

Of course, mixtures of the abovementioned silicones may also be present in the agents as contemplated herein. Exemplary silicones which can be used as contemplated herein have viscosities of from about 0.2 to about 2 mm²s⁻¹ at about 20° C., wherein silicones having viscosities of from about 0.5 to about 1 mm²s⁻¹ are particularly exemplary.

Particularly exemplary agents as contemplated herein contain one or more amino-functional silicones. Such silicones may, for example, be described by the formula

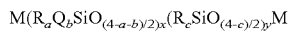

$M(R_aQ_bSiO_{(4-a-b)/2})_x(R_cSiO_{(4-c)/2})_yM$ wherein in the above formula R is a hydrocarbon or a hydrocarbon radical having from about 1 to about 6 carbon atoms, Q is a polar radical of the general formula —R¹HZ, wherein $R^1$ is a divalent linking group that is bonded to hydrogen and the radical Z, composed of carbon and hydrogen atoms, carbon, hydrogen and oxygen atoms or carbon, hydrogen and nitrogen atoms, and Z is an organic, amino-functional radical which contains at least one amino-functional group; "a" assumes values in the range of about 0 to about 2, "b" assumes values in the range of about 1 to about 3, "a"+"b" is less than or equal to about 3, and "c" is a number in the range from about 1 to about 3, and x is a number in the range of from about 1 to about 2,000, for example from about 3 to about 50, and most from about 3 to about 25, and y is a number in the range of about 20 to about 10,000, for example from about 125 to about 10,000, and most from about 150 to about 1,000, and M is a suitable silicone end group as known in the art, for example trimethylsiloxy. Non-limiting examples of the radicals represented by R include alkyl groups such as methyl, ethyl, propyl, isopropyl, isopropyl, butyl, isobutyl, amyl, isoamyl, hexyl, isohexyl and the like; alkenyl radicals such as vinyl, halovinyl, alkylvinyl, allyl, haloallyl, alkylallyl; cycloalkyl radicals such as cyclobutyl, cyclopentyl, cyclohexyl and the like; phenyl radicals, benzyl radicals, halogen hydrocarbon radicals such as 3-chloropropyl, 4-bromobutyl, 3,3,3-trifluoropropyl, chlorocyclohexyl, bromophenyl, chlorophenyl and the like, and sulfur containing radicals such as mercaptoethyl, mercaptopropyl, mercaptohexyl, mercaptophenyl and the like; R is an alkyl radical that contains from about 1 to about 6 carbon atoms, and most R is methyl. Examples of $R^1$ include methylene, ethylene, propylene, hexamethylene, decamethylene, —CH₂CH(CH₃)CH₂—, phenylene, naphthylene, —CH₂CH₂SCH₂CH₂—, —CH₂CH₂OCH₂—, —OCH₂CH₂—, —OCH₂ CH₂CH₂—, —CH₂CH(CH₃)C(O)OCH₂—, —(CH₂)₃ CC(O)OCH₂CH₂—, —C₆H₄C₆H₄—, —C₆H₄CH₂C₆H₄—; and —(CH₂)₃C(O)SCH₂CH₂—.

Z is an organic, amino-functional radical containing at least one functional amino group. A possible formula for Z is $NH(CH_2)_zNH_2$, wherein z is about 1 or more. Another possible formula for Z is —NH(CH₂)z(CH₂)zzNH, wherein both z and zz are independently about 1 or more, wherein this structure includes diamino ring structures such as piperazinyl. Z is most an —NHCH₂CH₂NH₂— radical. Another possible formula for Z is —N(CH₂)z(CH₂)zzNX₂ or —NX₂, wherein each X of X₂ is independently selected from the group including of hydrogen and alkyl groups having from about 1 to about 12 carbon atoms, and zz is about 0.

Q is most a polar, amino-functional radical of the formula —CH₂CH₂CH₂NHCH₂CH₂NH₂. In the formulas, "a" assumes values in the range of about 0 to about 2, "b" assumes values in the range of about 2 to about 3, "a"+"b" is less than or equal to about 3, and "c" is a number in the range of about 1 to about 3. The molar ratio of the $R_aQ_b SiO_{(4-a-b)/2}$ units to the $RcSiO_{(4-c)/2}$ units is in the range of from about 1:2 to about 1:65, for example from about 1:5 to about 1:65 and most from about 1:15 to about 1:20. When one or more silicones of the above formula are used, the various variable substituents in the above formula may be different for the various silicone components which are present in the silicone mixture.

Exemplary agents as contemplated herein are exemplified in that they contain an amino-functional silicone of the formula (Si-II)

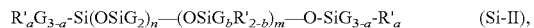

$R'_aG_{3-a}-Si(OSiG_2)_n—(OSiG_bR'_{2-b})_m—O-SiG_{3-a}-R'_a$ (Si-II), in which means:

G is —H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;

a stands for a number between about 0 and about 3, in particular about 0;

b stands for a number between about 0 and about 1, in particular about 1, m and n are numbers whose sum (m+n) is between about 1 and about 2000, for example between about 50 and about 150, wherein n assumes values from about 0 to about 1999 and in one embodiment from about 49 to about 149 and m assumes values from about 1 to about 2000, in particular from about 1 to about 10, R' is a monovalent radical selected from
Q-N(R")—CH$_2$—CH$_2$—N(R")$_2$
-Q-N(R")$_2$
-Q-N$^+$(R")$_3$A$^-$
-Q-N$^+$H(R")$_2$ A$^-$
-Q-N$^+$H$_2$(R")A$^-$
-Q-N(R")—CH$_2$—CH$_2$—N$^+$R"H$_2$A$^-$, wherein each Q stands for a chemical bond, CH$_2$—, —CH$_2$—CH$_2$—, —CH$_2$CH$_2$CH$_2$—, —C(CH$_3$)$_2$—, —CH$_2$CH$_2$CH$_2$CH$_2$—, —CH$_2$C(CH$_3$)$_2$—, —CH(CH$_3$)CH$_2$CH$_2$—, R' stands for identical or different radicals from the group —H, -phenyl, -benzyl, —CH$_2$—CH(CH$_3$)Ph, the C$_{1-20}$-alkyl radicals, for example —CH$_3$, —CH$_2$CH$_3$, —CH$_2$CH$_2$CH$_3$, —CH(CH$_3$)$_2$, —CH$_2$CH$_2$CH$_2$H$_3$, —CH$_2$CH(CH$_3$)$_2$, —CH(CH$_3$)CH$_2$CH$_3$, —C(CH$_3$)$_3$, and A represents an anion, which is selected from chloride, bromide, iodide or methosulfate.

Particularly exemplary agents as contemplated herein are exemplified in that they contain at least one amino-functional silicone of the formula (Si-IIa)

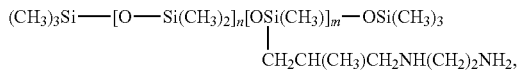

(Si-IIa)

wherein m and n are numbers whose sum (m+n) is between about 1 and about 2000, for example between about 50 and about 150, wherein n assumes values from about 0 to about 1999 and in one embodiment from about 49 to about 149 and m assumes values from about 1 to about 2000, in particular from about 1 to about 10.

These silicones are referred to as trimethylsilylamodimethicones according to the INCI declaration.

Also particularly exemplary are agents as contemplated herein which contain an amino-functional silicone of the formula (Si-IIb)

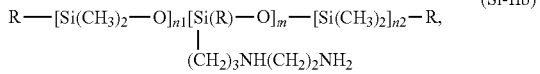

(Si-IIb)

wherein R stands for —OH, —O—CH$_3$ or a —CH$_3$ group and m, n1 and n2 are numbers whose sum (m+n1+n2) is between about 1 and about 2,000, for example between about 50 and about 150, wherein the sum (n1+n2) assumes values from about 0 to about 1999 and in one embodiment from about 49 to about 149 and m assumes values from about 1 to about 2000, in particular from about 1 to about 10.

These silicones are referred to as amodimethicones according to the INCI declaration.

Regardless of which amino-functional silicones are used, agents as contemplated herein which contain an amino-functional silicone whose amine number is above about 0.25 meq/g, for example above about 0.3 meq/g and in one embodiment above about 0.4 meq/g, are exemplary. The amine number stands for the milliequivalents of amine per gram of the amino-functional silicone. It can be determined by titration and also expressed in mg KOH/g.

Hair treatment agents as contemplated herein which are exemplary are exemplified in that they contain, based on their weight, from about 0.01 to about 20% by weight, for example from about 0.1 to about 10% by weight, such as from about 0.5 to about 7.5% by weight and in one embodiment from about 1 to about 5% by weight, of silicone(s).

With particular consideration, the agents as contemplated herein contain amino-functional silicone(s) with terminal hydroxy group(s). Some specific amino-functional silicone(s) having terminal hydroxyl group(s) have been found to be particularly useful in the agents of this present disclosure. These are described below.

Exemplary agents as contemplated herein are exemplified in that, based on their weight, they contain from about 0.01 to about 20% by weight, for example from about 0.1 to about 10% by weight, such as from about 0.5 to about 7.5% by weight and in one embodiment from about 1 to about 5% by weight, of at least one silicone of the following formula (Si-III)

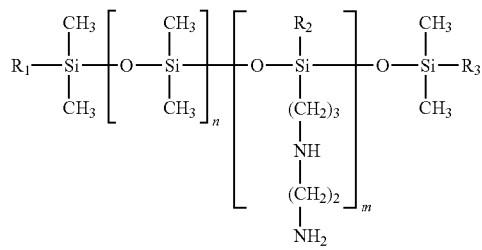

(Si-III)

in which
m and n mean numbers chosen so that the sum (n+m) ranges from about 1 to about 1000,
n is a number in the range of from about 0 to about 999 and m is a number in the range of from about 1 to about 1000,
R1, R2 and R3, which are the same or different, mean a hydroxy group or a C1-4 alkoxy group,
wherein at least one of R1 to R3 means a hydroxy group;

Exemplary agents as contemplated herein are exemplified in that, based on their weight, they contain from about 0.01 to about 20% by weight, for example from about 0.1 to about 10% by weight, such as from about 0.5 to about 7.5% by weight and in one embodiment from about 1 to about 5% by weight, of at least one silicone of the following formula (Si-IV)

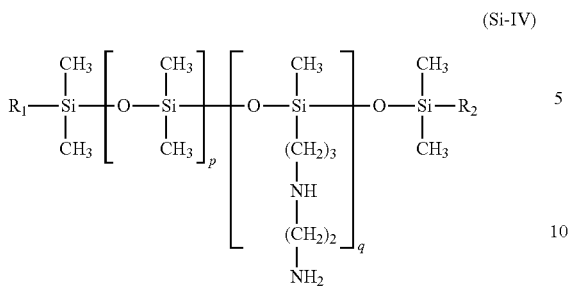

(Si-IV)

in which
p and q mean numbers chosen so that the sum (p+q) ranges from about 1 to about 1000,
p is a number in the range of from about 0 to about 999 and q is a number in the range of from about 1 to about 1000,
R1 and R2 which are different mean a hydroxy group or a C1-4 alkoxy group, wherein at least one of the group R1 to R2 means a hydroxy group.

The silicones of the formulas (Si-III) and (Si-IV) differ by the grouping on the Si atom which carries the nitrogen-containing group: In formula (Si-III), R2 means a hydroxy group or a C1-4 alkoxy group while the radical in formula (Si-IV) is a methyl group. The individual Si groupings, which are identified by the indices m and n or p and q, need not be present as blocks, but rather the individual units can also be present in statistical distribution, i.e., in the formulas (Si-III) and (Si) IV), not every R1-Si(CH3)2 group is bonded to an —[O—Si(CH3)2] group.

In the method as contemplated herein, pretreatment agents which contain at least one silicone of the formula (Si-V) have proven particularly effective with regard to the desired effects:

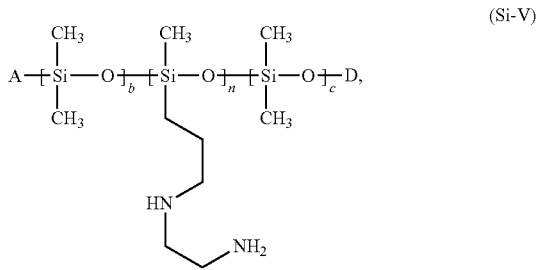

(Si-V)

in which
A stands for a group —OH, —O—Si(CH3)3, —O—Si(CH3)2OH, —O—Si(CH3)2OCH3,
D stands for a group —H, —Si(CH3)3, —Si(CH3)2OH, —Si(CH3)2OCH3,
b, n and c stand for integers between about 0 and about 1000,
with the stipulations
n>about 0 and b+c>about 0
at least one of the conditions A=—OH or D=—H is fulfilled.

Hair treatment agents as contemplated herein, which, based on their weight, contain from about 0.01 to about 20% by weight, for example from about 0.1 to about 10% by weight, in an example from about 0.5 to about 7.5% by weight, and in one embodiment from about 1 to about 5% by weight, of at least one silicone of the formula (Si-V):

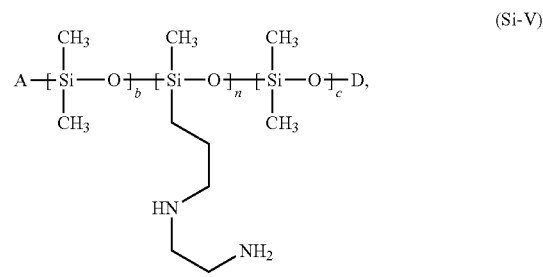

(Si-V)

in which
A stands for a group —OH, —O—Si(CH3)3, —O—Si(CH3)2OH, —O—Si(CH3)2OCH3,
D stands for a group —H, —Si(CH3)3, —Si(CH3)2OH, —Si(CH3)2OCH3,
b, n and c stand for integers between about 0 and about 1000,
with the stipulations
n>about 0 and b+c>about 0
at least one of the conditions A=—OH or D=—H is fulfilled,
are therefore exemplary as contemplated herein.

In the abovementioned formula (Si-V), the individual siloxane units having the indices b, c and n are statistically distributed, i.e., it does not necessarily have to be block copolymers.

Other particularly suitable silicones are 4-morpholinomethyl substituted. Hair treatment agents as contemplated herein, which, based on their weight, contain from about 0.01 to about 20% by weight, for example from about 0.1 to about 10% by weight, in an example from about 0.5 to about 7.5% by weight, and in one embodiment from about 1 to about 5% by weight, of at least one 4-morpholinomethyl-substituted silicone of the formula (Si-VI),

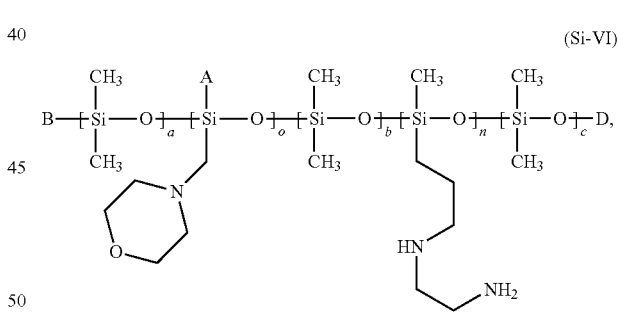

(Si-VI)

in which
A stands for a structural unit (i) bonded via an —O—

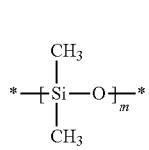

(i)

or an oligomeric or polymeric radical which is bonded via an —O— and contains structural units of the formula (i) or for —OH,
stands for a bond to the structural unit (i) or for an end group B (Si-bonded) or D (O-bonded), B stands for a group —OH, —O—Si(CH$_3$)$_3$, —O—Si(CH$_3$)$_2$OH, —O—Si(CH$_3$)$_2$OCH$_3$, D stands for a group —H, —Si(CH$_3$)$_3$, —Si(CH$_3$)$_2$OH, —Si(CH$_3$)$_2$OCH$_3$, a, b and c stand for integers between about 0 and about 1000, with the stipulation that a+b+c>about 0 m, n and o stand for integers between about 1 and about 1000.

with the stipulation that at least one of the conditions B=—OH or D=—H is satisfied, are particularly exemplary.

Structural formula (Si-VI) is intended to make it clear that the siloxane groups n and o do not necessarily have to be bonded directly to an end grouping B or D. Rather, in exemplary formulas (Si-VI) a>about 0 or b>about 0 and in one embodimently exemplary formulas (Si-VI) a>about 0 and b>about 0, i.e., the terminal grouping B or D, is bonded to a dimethylsiloxy grouping. Also in formula (Si-VI), the siloxane units a, b, c, n and o are statistically distributed.

The silicones used as contemplated herein represented by formula (Si-VI) may be trimethylsilyl-terminated (D or B=—Si(CH$_3$)$_3$), but they may also be dimethylsilylhydroxy-terminated on two sides or dimethylsilylhydroxy- and dimethylsilylmethoxy-terminated on one side. Silicones in an example used in the context of the present disclosure are selected from silicones in which are meant B=—O—Si(CH$_3$)$_2$OH and D=—Si(CH$_3$)$_3$ B=—O—Si(CH$_3$)$_2$OH and D=—Si(CH$_3$)$_2$OH B=—O—Si(CH$_3$)$_2$OH and D=—Si(CH$_3$)$_2$OCH$_3$ B=—O—Si(CH$_3$)$_3$ and D=—Si(CH$_3$)$_2$OH B=—O—Si(CH$_3$)$_2$OCH$_3$ and D=—Si(CH$_3$)$_2$OH These silicones lead to exorbitant improvements in the hair properties of the hairs treated with the agents as contemplated herein, in particular to a significantly improved protection in the case of oxidative treatment. Also, in formula (Si-VI), the radical A may stand for a structural unit (i) bonded via an —O— or an oligomeric or polymeric radical containing structural units of the formula (i) bonded via an —O— or for —OH.

Thus, formula (Si-VI) is specified to one of the formulas (Si-VIa), (Si-VIb) or (Si-VIc):

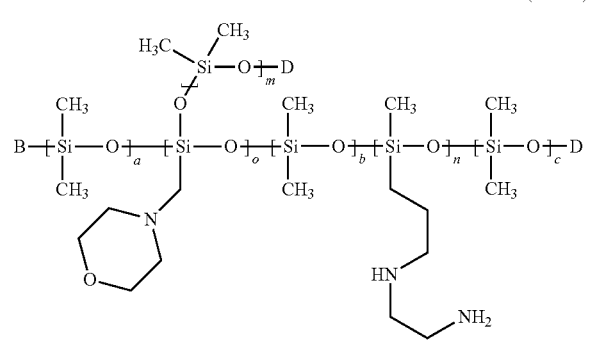

(Si-VIa)

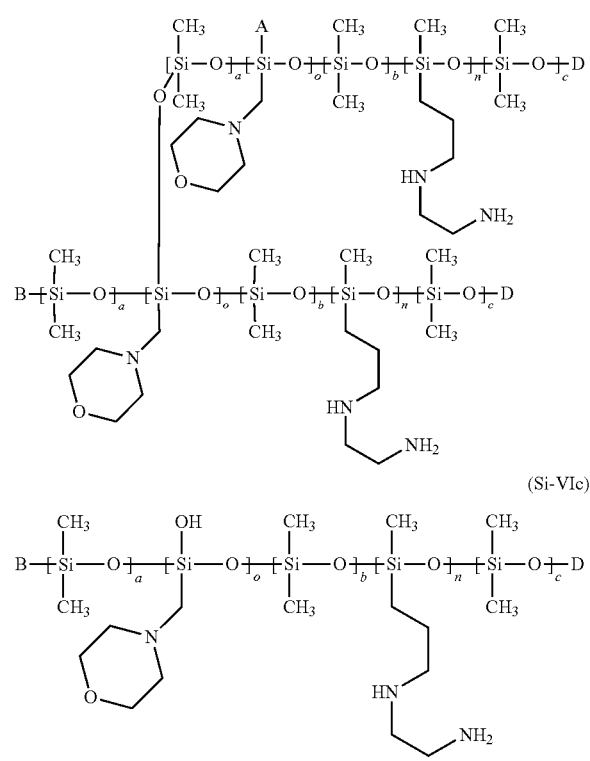

(Si-VIb)

(Si-VIc)

Regardless of the type of the aminofunctional silicone(s) used with terminal hydroxyl group(s), the agents as contemplated herein contain the silicone(s) in the form of an emulsion, such as in the form of a microemulsion.

It has been shown that the effect of the silicones used in the agents as contemplated herein can be increased even if certain nonionic components are also used in the agents. In addition, these nonionic components have positive effects on the storage stability of the agents. Nonionic components which are particularly useful here are ethoxylates of decanol, undecanol, dodecanol, tridecanol, etc. Ethoxylated tridecanols which are incorporated with particular consideration in the inventive agents have proven particularly suitable. Agents as contemplated herein which are particularly exemplary are exemplified in that, based on their weight, they contain from about 0.00001 to about 5% by weight, for example from about 0.0001 to about 3.5% by weight, in an example from about 0.001 to about 2% by weight, such as from about 0.01 to about 1% by weight, and in one embodiment from about 0.1 to about 0.5% by weight, of branched, ethoxylated tridecanol (INCI name: trideceth-5) or α-isotridecyl-ω-hydroxypolyglycol ether (INCI name: trideceth-10) or mixtures thereof.

The hair treatment agents contain the active ingredients described above in a cosmetically acceptable carrier. For the purposes of the present disclosure, this is understood as meaning an aqueous or aqueous-alcoholic carrier.

The cosmetic carrier contains at least about 50% by weight, such as at least about 60% by weight, such as at least about 70% by weight and in one embodiment at least about 75% by weight, of water.

Furthermore, the cosmetic carrier may contain from about 0.01 to about 40% by weight, for example from about 0.05 to about 30% by weight and in one embodiment from about 0.1 to about 20% by weight, of at least one alcohol.

Suitable alcohols are, for example, ethanol, ethyl diglycol, 1-propanol, 2-propanol, isopropanol, 1,2-propylene glycol, glycerol, diglycerol, triglycerol, 1-butanol, 2-butanol, 1,2-butanediol, 1,3-butanediol, 1-pentanol, 2-pentanol, 1,2-pentanediol, 1,5-pentanediol, 1, hexanol, 2-hexanol, 1,2-hexanediol, 1,6-hexanediol, polyethylene glycols, sorbitol, sorbitan, benzyl alcohol or mixtures of these alcohols.

Particularly exemplary are the water-soluble alcohols. Particularly exemplary are ethanol, 1,2-propylene glycol, glycerol, benzyl alcohol and mixtures of these alcohols.

For a very good (head) skin compatibility of the hair treatment agents as contemplated herein, it is advantageous when said agents have a slightly acidic pH value.

It has been found that the agents as contemplated herein have a particularly good skin tolerance and mildness in a pH range from about 4.2 to about 5.8.

In a first exemplary embodiment, the hair treatment agents as contemplated herein therefore have a pH value in the range from about 4.2 to about 5.8, such as from about 4.25 to about 5.6, in an example from about 4.3 to about 5.5, very from about 4.35 to about 5.4, and in one embodiment from about 4.4 to about 5.3.

The hair treatment agents as contemplated herein may contain vegetable oils, vegetable butters and/or vegetable waxes. These vegetable oil components give the hair improved combability and manageability and increase the hair shine.

Suitable vegetable oil components include natural (vegetable) oils and/or butters, which commonly contain triglycerides and mixtures of triglycerides.

Exemplary natural oils are coconut oil, (sweet) almond oil, walnut oil, peach kernel oil, apricot kernel oil, argan oil, avocado oil, tea tree oil, soybean oil, sesame oil, sunflower oil, tsubaki oil, evening primrose oil, rice bran oil, palm kernel oil, mango seed oil, marula oil, lady's smock oil, thistle oil, macadamia nut oil, grape seed oil, amaranth seed oil, bamboo oil, olive oil, wheat germ oil, pumpkin seed oil, mallow oil, hazelnut oil, safflower oil, canola oil, sasanqua oil, jojoba oil, rambutan oil, cocoa butter and/or shea butter.

Carnauba waxes, beeswaxes and/or candelilla waxes may be used as suitable natural or vegetable waxes.

Particularly exemplary vegetable oil components are (sweet) almond oil, peach kernel oil, apricot kernel oil, amaranth seed oil, argan oil, olive oil, jojoba oil, cocoa butter and/or shea butter.

Apricot kernel oil, argan oil, olive oil and/or jojoba oil are particularly exemplary.

In a exemplary embodiment, the hair treatment agents as contemplated herein contain coconut oil, (sweet) almond oil, walnut oil, peach kernel oil, apricot kernel oil, argan oil, avocado oil, tea tree oil, soybean oil, sesame oil, sunflower oil, tsubaki oil, evening primrose oil, rice bran oil, palm kernel oil, mango seed oil, marula oil, meadowfoam seed oil, thistle oil, macadamia nut oil, grapeseed oil, amaranth seed oil, bamboo oil, olive oil, wheat germ oil, pumpkin seed oil, mallow oil, hazelnut oil, safflower oil, canola oil, sasanqua oil, jojoba oil, rambutan oil, cocoa butter and/or shea butter.

Within this embodiment, it is particularly exemplary when the hair treatment agents as contemplated herein contain (sweet) almond oil, peach kernel oil, apricot kernel oil, amaranth seed oil, argan oil, olive oil, jojoba oil, cocoa butter and/or shea butter.

The proportion by weight of the at least one vegetable oil, the vegetable butter and/or the vegetable wax in the total weight of the hair treatment agents as contemplated herein is from about 0.02 to about 2.50% by weight, such as from about 0.03 to about 2.00% by weight, in an example from about 0.04 to about 1.50% by weight and in one embodiment from about 0.05 to about 1.00% by weight.

In addition to the abovementioned constituents, the hair treatment agents as contemplated herein may contain, in a further exemplary embodiment, for further increasing the care properties of the agents, at least one further hair conditioning active ingredient which may be selected from the group of
protein hydrolysates,
vitamins,
plant extracts and/or
glycerol.

Suitable protein hydrolysates are understood to be product mixtures which can be obtained by acid, alkaline or enzymatically catalyzed degradation of proteins.

Protein hydrolysates of plant, animal and/or marine origin may be used.

Animal protein hydrolysates are, for example, elastin, collagen, keratin, silk and milk protein protein hydrolysates, which may also exist in the form of salts. Such products are marketed, for example, under the trademarks Dehylan® (Cognis), Promois® (Interorgana), Collapuron® (Cognis), Nutrilan® (Cognis), Gelita sol® (Deutsche Gelatine Fabriken Stoess & Co), Lexein® (Inolex) and Kerasol® (Croda).

Consideration is given to protein hydrolysates of plant origin, e.g., soybean, almond, rice, pea, potato and wheat protein hydrolysates. Such products are, for example, available under the trademarks Gluadin® (Cognis), DiaMin® (Diamalt), Lex® (Inolex) and Crotein® (Croda).

The proportion by weight of the protein hydrolysate(s) in the total weight of the hair treatment agents is from about 0.01 to about 5% by weight, such as from about 0.025 to about 3% by weight and in one embodiment from about 0.05 to about 2% by weight.

Suitable vitamins are understood to mean the following vitamins, provitamins and vitamin precursors and their derivatives:

Vitamin A: the group of substances called vitamin A includes retinol (vitamin $A_1$) and 3,4-didehydroretinol (vitamin $A_2$). β Carotene is the provitamin of retinol. For example, vitamin A acid and its esters, vitamin A aldehyde and vitamin A alcohol and its esters such as the palmitate and the acetate are considered a vitamin A component.

Vitamin B: the vitamin B group or the vitamin B complex, among others, include
vitamin $B_1$ (thiamine)
vitamin $B_2$ (riboflavin)
vitamin $B_3$. The compounds nicotinic acid and nicotinamide (niacinamide) are sometimes conducted under this name.
Vitamin $B_5$ (pantothenic acid and panthenol). Panthenol is used as part of this group. Useful derivatives of panthenol are, in particular, the esters and ethers of panthenol, pantolactone and also cationically derivatized panthenols. Individual representatives are, for example, panthenol triacetate, panthenol monoethyl ether and its monoacetate, and cationic panthenol derivatives.
Vitamin $B_6$ (pyridoxine and pyridoxamine and pyridoxal).

Vitamin C (ascorbic acid): use in the form of palmitic acid ester, glucosides or phosphates may be exemplary. Use in combination with tocopherols may also be exemplary.

Vitamin E (tocopherols, in particular α-tocopherol).

Vitamin F: the term "vitamin F" is sometimes understood as meaning essential fatty acids, in particular linoleic acid, linolenic acid and arachidonic acid.

Vitamin H: The compound (3aS, 4S, 6aR)-2-oxohexahydrothienol [3,4-d] imidazole-4-valeric acid is called vitamin H, for which, however in the meantime, is accepted under the trivial name biotin.

Particular consideration is given to vitamins, provitamins and vitamin precursors from the groups A, B, E and H. Particular consideration is given to nicotinamide, biotin, pantolactone and/or panthenol.

The proportion by weight of the vitamin(s), vitamin derivative(s), and/or the vitamin precursor(s) in the total weight of the hair treatment agent is from about 0.001 to about 2% by weight, in an example from about 0.005 to about 1% by weight and in one embodiment from about 0.01 to about 0.5% by weight.

Suitable plant extracts are understood to be extracts that can be made from any part of a plant. Sometimes, these extracts are prepared by extraction of the entire plant. However, in individual cases it may also be exemplary to make the extracts exclusively from flowers and/or leaves of the plant. Particularly suitable are the extracts of green tea, oak bark, stinging nettle, witch hazel, hops, chamomile, burdock root, horsetail, hawthorn, linden, lychee, almond, aloe vera, spruce needle, horse chestnut, sandalwood, juniper, coconut, mango, apricot, lime, wheat, kiwi, melon, orange, grapefruit, sage, rosemary, birch, mallow, lady's smock, thyme, yarrow, thyme, balm, restharrow, coltsfoot, marshmallow, ginseng, ginger root, Echinacea purpurea, olive, Boerhavia diffusa roots, fennel and celery.

Particularly exemplary for use in the compositions as contemplated herein are the extracts of green tea, stinging nettle, witch hazel, chamomile, aloe vera, ginseng, Echinacea purpurea, olive and/or Boerhavia diffusa roots.

Water, alcohols and mixtures thereof can be used as extraction agent for the preparation of said plant extracts. Among the alcohols are exemplary lower alcohols such as ethanol and isopropanol, but in particular polyhydric alcohols such as ethylene glycol and propylene glycol, both as sole extraction agent and in mixture with water. Plant extracts based on water/propylene glycol in a ratio of from about 1:10 to about 10:1 have proven to be particularly suitable.

The plant extracts can be used both in pure and in diluted form. If they are used in diluted form, they sometimes contain from about 2 to about 80% by weight of active substance and, as solvent, the extraction agent or extraction agent mixture used in their extraction.

The plant extracts may be used in the hair treatment agents as contemplated herein (based on the total weight of the agent) in an amount of from about 0.01 to about 10% by weight, such as from about 0.05 to about 7.5% by weight and in one embodiment from about 0.1 to about 5% by weight.

Glycerol may be added to the hair cleansing and conditioning agents separately in an amount of up to about 10% by weight (based on the total weight of the agent). However, it may also be a constituent of the aforementioned aqueous-alcoholic carrier.

It has been found that the hair treatment agents as contemplated herein are also suitable for use as an anti-dandruff preparation.

The total weight of anti-dandruff agents in the total weight of the hair treatment agent may be from about 0.01 to about 10% by weight, such as from about 0.025 to about 7.5% by weight, in an example from about 0.05 to about 5% by weight and in one embodiment from about 0.075 to about 3% by weight.

Suitable anti-dandruff active ingredients may be selected from piroctone olamine, climbazole, zinc pyrithione, ketoconazole, salicylic acid, sulfur, selenium sulfide, tar preparations, undecenoic acid derivatives, burdock root extracts, poplar extracts, stinging nettle extracts, walnut shell extracts, birch extracts, willow bark extracts, rosemary extracts and/or arnica extracts.

Exemplary are climbazole, zinc pyrithione and piroctone olamine.

Further active ingredients, auxiliaries and additives which may be contained in the hair treatment agents as contemplated herein are, for example:

humectants,
perfumes,
UV filters,
thickening agents such as gelatin or vegetable gums, for example agar-agar, guar gum, alginates, xanthan gum, gum arabic, karaya gum, locust bean gum, linseed gums, dextrans, cellulose derivatives, such as methyl cellulose, hydroxyalkyl cellulose and carboxymethyl cellulose, starch fractions and derivatives such as, amylose, amylopectin and dextrins, clays and phyllosilicates such as bentonite or fully synthetic hydrocolloids such as polyvinyl alcohol, the Ca, Mg or Zn soaps,
structurants such as maleic acid and lactic acid,
dimethyl isosorbide,
cyclodextrins,
fiber-structure-improving active ingredients, in particular mono-, di- and oligosaccharides such as, for example, glucose, galactose, fructose, fruit sugar and lactose,
dyes for coloring the agent,
active ingredients such as bisabolol and/or allantoin,
complexing agents such as EDTA, NTA, β alanine diacetic acid and phosphonic acids,
ceramides. Ceramides are understood as meaning N-acyl-sphingosine (fatty acid amides of sphingosine) or synthetic analogs of such lipids (so-called pseudo-ceramides),
propellants such as propane-butane mixtures, $N_2O$, dimethyl ether, $CO_2$ and air,
antioxidants,
additional viscosity regulators, such as salts (NaCl).

The agents as contemplated herein are so-called rinse-off products, i.e., they are rinsed out of the hair again after a certain residence time. This residence time is less than one hour, i.e., the consumer does not leave the products in the hair until the next hair wash.

Another subject of the present disclosure is therefore a method for hair treatment in which an agent as contemplated herein is applied to dry or damp hair, left there for a period of from about 30 to about 300 seconds and then rinsed out.

The agents as contemplated herein lead to a significantly increased split reduction.

Another subject of the present disclosure is therefore the use of mixtures of
a) at least one anteiso fatty acid quat,
b) alkyldimethylammonium hydroxypropyl hydrolyzed keratin
to increase the hair conditioning properties of hair treatment agents.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

Examples (all Specified in % by Weight)

Hair Shampoos:

|  | 1 | 2 | 3 | 4 | 5 | 6 |
|---|---|---|---|---|---|---|
| Sodium laureth sulfate | 14.0 | 14.0 | 14.0 | 14.0 | 14.0 | 14.0 |
| Disodium cocoamphodiacetate | 7.0 | 7.0 | 7.0 | 7.0 | 7.0 | 7.0 |
| Polyquaternium-10 | 1.5 | 1.5 | 1.5 | 1.5 | 1.5 | 1.5 |
| Citric acid | 0.5 | 0.5 | 0.5 | 0.5 | 0.5 | 0.5 |
| NaOH | 0.1 | 0.1 | 0.1 | 0.1 | 0.1 | 0.1 |
| Sodium benzoate | 0.5 | 0.5 | 0.5 | 0.5 | 0.5 | 0.5 |
| Panthenol 75% | 0.5 | 0.5 | 0.5 | 0.5 | 0.5 | 0.5 |
| Tocopheryl acetate | 0.2 | 0.2 | 0.2 | 0.2 | 0.2 | 0.2 |
| C10-40 isoalkylamidopropyl-ethyldimonium ethosulfates | 0.2 | 0.15 | 0.2 | 0.1 | 0.2 | 0.05 |
| Steardimonium hydroxypropyl hydrolyzed keratin | 0.2 | 0.2 | 0.15 | 0.2 | 0.1 | 0.05 |
| Hydrolyzed keratin | 0.1 | 0.1 | 0.1 | 0.1 | 0.1 | 0.1 |
| PEG-40 hydrogenated castor oil | 0.5 | 0.5 | 0.5 | 0.5 | 0.5 | 0.5 |
| Sodium chloride | 1.5 | 1.5 | 1.5 | 1.5 | 1.5 | 1.5 |
| Water, preservative and possibly perfume oils | ad 100 | ad 100 | ad 100 | ad 100 | ad 100 | ad 100 |

Intensive Treatments:

|  | 1 | 2 | 3 | 4 | 5 | 6 |
|---|---|---|---|---|---|---|
| Quaternium-87 | 3.5 | 3.5 | 3.5 | 3.5 | 3.5 | 3.5 |
| Glyceryl stearate | 1.0 | 1.0 | 1.0 | 1.0 | 1.0 | 1.0 |
| Cetearyl alcohol | 7.0 | 7.0 | 7.0 | 7.0 | 7.0 | 7.0 |
| Lecithin | 0.4 | 0.4 | 0.4 | 0.4 | 0.4 | 0.4 |
| Isopropyl myristate | 1.0 | 1.0 | 1.0 | 1.0 | 1.0 | 1.0 |
| Distearoylethyl hydroxyethyl-monium methosulfate | 2.0 | 2.0 | 2.0 | 2.0 | 2.0 | 2.0 |
| Paraffinum liquidum | 1.0 | 1.0 | 1.0 | 1.0 | 1.0 | 1.0 |
| Methylparaben | 0.4 | 0.4 | 0.4 | 0.4 | 0.4 | 0.4 |
| Citric acid | 0.7 | 0.7 | 0.7 | 0.7 | 0.7 | 0.7 |
| C10-40 isoalkylamidopropyl-ethyldimonium ethosulfates | 0.2 | 0.15 | 0.2 | 0.1 | 0.2 | 0.05 |
| Steardimonium hydroxypropyl hydrolyzed keratin | 0.2 | 0.2 | 0.15 | 0.2 | 0.1 | 0.05 |
| Panthenol 75% | 0.5 | 0.5 | 0.5 | 0.5 | 0.5 | 0.5 |
| Hydrolyzed keratin | 0.1 | 0.1 | 0.1 | 0.1 | 0.1 | 0.1 |
| Niacinamide | 0.2 | 0.2 | 0.2 | 0.2 | 0.2 | 0.2 |
| Water, preservative, accompanying substances and possibly perfume oils | ad 100 | ad 100 | ad 100 | ad 100 | ad 100 | ad 100 |

Hair Treatments

|  | 1 | 2 | 3 | 4 | 5 | 6 |
|---|---|---|---|---|---|---|
| Cetearyl alcohol | 7.0 | 7.0 | 7.0 | 7.0 | 7.0 | 7.0 |
| Quaternium-87 | 0.9 | 0.9 | 0.9 | 0.9 | 0.9 | 0.9 |
| Cetrimonium chloride | 1.5 | 1.5 | 1.5 | 1.5 | 1.5 | 1.5 |
| Distearoylethyl hydroxyethyl-monium methosulfate | 2.0 | 2.0 | 2.0 | 2.0 | 2.0 | 2.0 |
| Polyquaternium-10 | 0.1 | 0.1 | 0.1 | 0.1 | 0.1 | 0.1 |
| Baobab seed oil | 0.1 | 0.1 | 0.1 | 0.1 | 0.1 | 0.1 |
| Polyquaternium-37 | 0.4 | 0.4 | 0.4 | 0.4 | 0.4 | 0.4 |
| Hydrolyzed keratin | 0.5 | 0.5 | 0.5 | 0.5 | 0.5 | 0.5 |
| Glycol distearate | 1.0 | 1.0 | 1.0 | 1.0 | 1.0 | 1.0 |
| Citric acid | 1.5 | 1.5 | 1.5 | 1.5 | 1.5 | 1.5 |
| Dimethicone | 1.0 | 1.0 | 1.0 | 1.0 | 1.0 | 1.0 |
| C10-40 isoalkylamidopropyl-ethyldimonium ethosulfates | 0.2 | 0.15 | 0.2 | 0.1 | 0.2 | 0.05 |
| Steardimonium hydroxypropyl hydrolyzed keratin | 0.2 | 0.2 | 0.15 | 0.2 | 0.1 | 0.05 |
| Water, preservative, accompanying substances and possibly perfume oils | ad 100 | ad 100 | ad 100 | ad 100 | ad 100 | ad 100 |

Hair Conditioners

|  | 1 | 2 | 3 | 4 | 5 | 6 |
|---|---|---|---|---|---|---|
| Cetearyl alcohol | 5.0 | 5.0 | 5.0 | 5.0 | 5.0 | 5.0 |
| Quaternium-87 | 0.75 | 0.75 | 0.75 | 0.75 | 0.75 | 0.75 |
| Behentrimonium chloride | 1.0 | 1.0 | 1.0 | 1.0 | 1.0 | 1.0 |
| Behenoyl PG trimonium chloride | 1.5 | 1.5 | 1.5 | 1.5 | 1.5 | 1.5 |
| Glycol distearate | 1.0 | 1.0 | 1.0 | 1.0 | 1.0 | 1.0 |
| Distearoylethyl hydroxyethyl-monium methosulfate | 0.3 | 0.3 | 0.3 | 0.3 | 0.3 | 0.3 |
| Amodimethicone/morpholinomethyl silsesquioxane copolymer | 0.1 | 0.1 | 0.1 | 0.1 | 0.1 | 0.1 |
| Citric acid | 0.5 | 0.5 | 0.5 | 0.5 | 0.5 | 0.5 |
| Shea butter | 1.5 | 1.5 | 1.5 | 1.5 | 1.5 | 1.5 |
| Lactic acid | 0.1 | 0.1 | 0.1 | 0.1 | 0.1 | 0.1 |
| Magnesium chloride | 0.5 | 0.5 | 0.5 | 0.5 | 0.5 | 0.5 |
| C10-40 isoalkylamidopropyl-ethyldimonium ethosulfates | 0.2 | 0.15 | 0.2 | 0.1 | 0.2 | 0.05 |
| Steardimonium hydroxypropyl hydrolyzed keratin | 0.2 | 0.2 | 0.15 | 0.2 | 0.1 | 0.05 |
| Water, preservative, accompanying substances and possibly perfume oils | ad 100 | ad 100 | ad 100 | ad 100 | ad 100 | ad 100 |

The invention claimed is:

1. A hair conditioner comprising:
   about 5.0% by weight Cetearyl alcohol;
   about 0.75% by weight Quaternium-87;
   about 1.0% by weight Behentrimonium chloride;
   about 1.5% by weight Behenoyl PG trimonium chloride;
   about 1.0% by weight Glycol distearate;
   about 0.3% by weight Distearoylethyl hydroxyethyl-monium methosulfate;
   about 0.1% by weight Amodimethicone/morpholinomethyl silsesquioxane copolymer;
   about 0.5% by weight Citric acid;
   about 1.5% by weight Shea butter;
   about 0.1% by weight Lactic acid;
   about 0.5% by weight Magnesium chloride;
   about 0.05-2% by weight $C_{10}$-$C_{40}$ isoalkylamidopropyl-ethyldimonium ethosulfates; and
   about 0.05-2% by weight steardimonium hydroxypropyl hydrolyzed keratin.

* * * * *